US00PP33529P2

(12) United States Plant Patent
Van Dijk

(10) Patent No.: US PP33,529 P2
(45) Date of Patent: Sep. 28, 2021

(54) ***ANTHURIUM* PLANT NAMED 'ANTHFYSAN'**

(50) Latin Name: ***Anthurium andraeanum* L.**
Varietal Denomination: ANTHFYSAN

(71) Applicant: ANTHURA B.V., Bleiswijk (NL)

(72) Inventor: Jan Van Dijk, Bleiswijk (NL)

(73) Assignee: Anthura B.V., Bleiswijk (NL)

( * ) Notice: Subject to any disclaimer, the term of this patent is extended or adjusted under 35 U.S.C. 154(b) by 0 days.

(21) Appl. No.: 16/974,382

(22) Filed: Jan. 6, 2021

(51) Int. Cl.
*A01H 5/02* (2018.01)
*A01H 6/00* (2018.01)

(52) U.S. Cl.
USPC ..... Plt./365
CPC ..... *A01H 6/00* (2018.05)

(58) Field of Classification Search
USPC ..... Plt./365
CPC ..... A01H 6/00
See application file for complete search history.

(56) References Cited

PUBLICATIONS

UPOV hit on *Anthurium* plant named 'ANTHFYSAN', QZ PBR 2018/2884, filed Nov. 1, 2018.*

* cited by examiner

*Primary Examiner* — Anne Marie Grunberg
(74) *Attorney, Agent, or Firm* — Jondle & Associates, P.C.

(57) ABSTRACT

A new *Anthurium* plant named 'ANTHFYSAN' particularly distinguished by having very shiny and weakly blistered, dark red, cordate, and durable spathes that retain the original color for a very long period of time, dark green-red and cordate, durable leaves, white spadices with yellow and greenish-yellow tips, early and rich flowering continuously throughout the year, and a plant height of 34.0 cm to 39.0 cm is disclosed.

3 Drawing Sheets

Genus and species: *Anthurium andraeanum* L.
Variety denomination: 'ANTHFYSAN'.

BACKGROUND OF THE NEW PLANT

The present invention comprises a new and distinct variety of *Anthurium*, botanically known as *Anthurium andraeanum* L., and hereinafter referred to by the variety name 'ANTHFYSAN'. The new *Anthurium* plant is a product of a planned breeding program conducted by the inventor in Bleiswijk, the Netherlands. The objective of this breeding program was to create a new plant with a height of 34.0 cm to 39.0 cm having very shiny and weakly blistered, dark red, cordate, and durable spathes.

The new variety originated from a cross-pollination made in May 2010 in Bleiswijk, the Netherlands. The female parent was a brown *Anthurium* pot plant designated '16704-02' (unpatented), and the male parent was a red *Anthurium* pot plant designated '20037-02' (unpatented).

A single plant was selected from the progeny of the stated cross in June 2012. Asexual reproduction of the new variety by tissue culture in 2016 in Bleiswijk, the Netherlands, has demonstrated that the new variety reproduces true to type with all of the characteristics, as herein described, firmly fixed and retained through successive generations.

Community Plant Variety Rights for this variety have been applied for in the European Union on Nov. 1, 2018 (Application no. 2018/2884), by Applicant who obtained the subject matter disclosed directly from the inventor. 'ANTHFYSAN' has not been made publicly available or sold anywhere in the world prior to the effective filing date of this application with the exception of sales or disclosures made one year or less before the effective filing date of this claimed invention by Applicant who obtained 'ANTHFYSAN' directly from the inventor.

SUMMARY OF THE INVENTION

The following are the most outstanding and distinguishing characteristics of this new variety when grown under normal horticultural practices in Bleiswijk, the Netherlands:

1) Very shiny, weakly blistered, dark red, cordate spathes;
2) White spadices with yellow and greenish-yellow tips;
3) Dark green-red, cordate leaves; and
4) Position of spathe compared to leaves is slightly below.

DESCRIPTION OF THE PHOTOGRAPHS

This new *Anthurium* plant is illustrated by the accompanying photographs which show the overall plant habit including blooms and foliage of the plant; the colors shown are as true as can be reasonably obtained by conventional photographic procedures. The photographs arc of a 44-week-old plant grown in a greenhouse in Bleiswijk, the Netherlands, in November 2020. Colors in the photographs may differ from the color values cited in the detailed botanical description, which accurately describe the actual colors of the new variety.

DESCRIPTION OF THE NEW VARIETY

Figure 1:
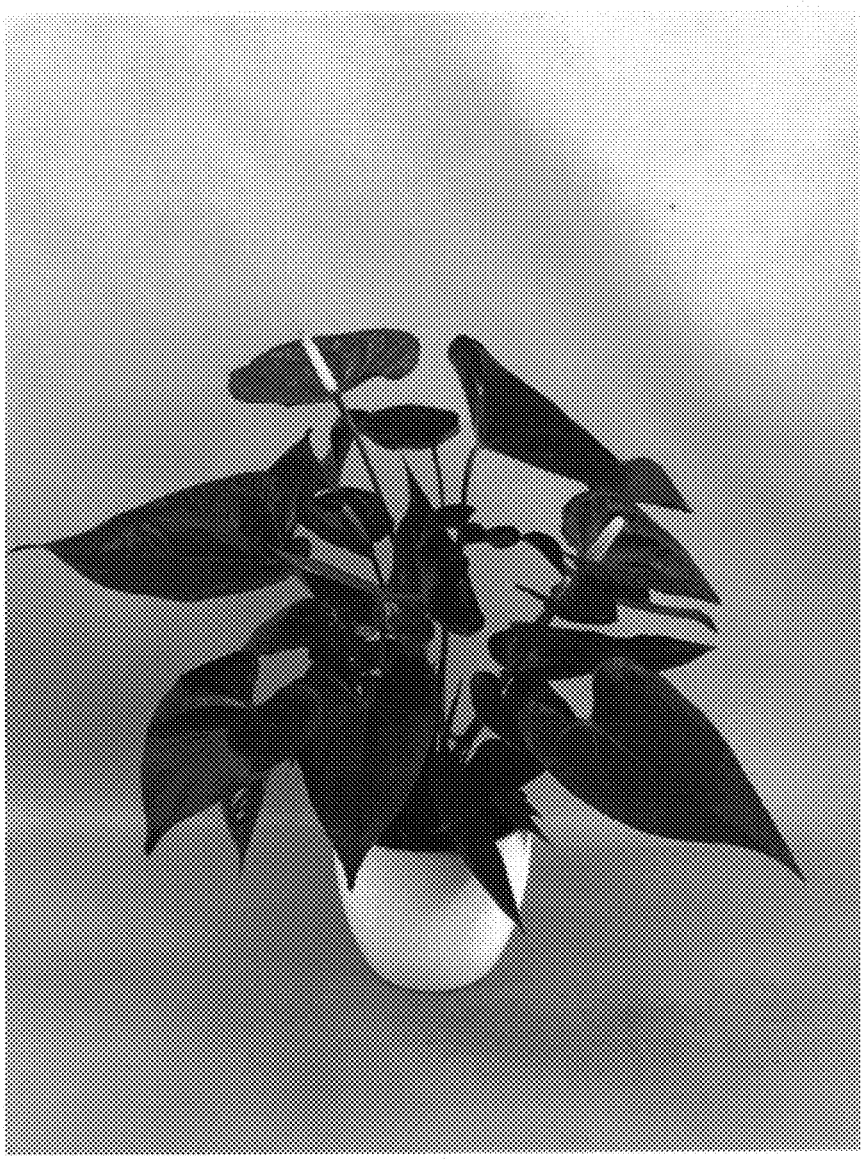
FIG. 1 shows the overall plant habit, including blooms and foliage.
Figure 2:
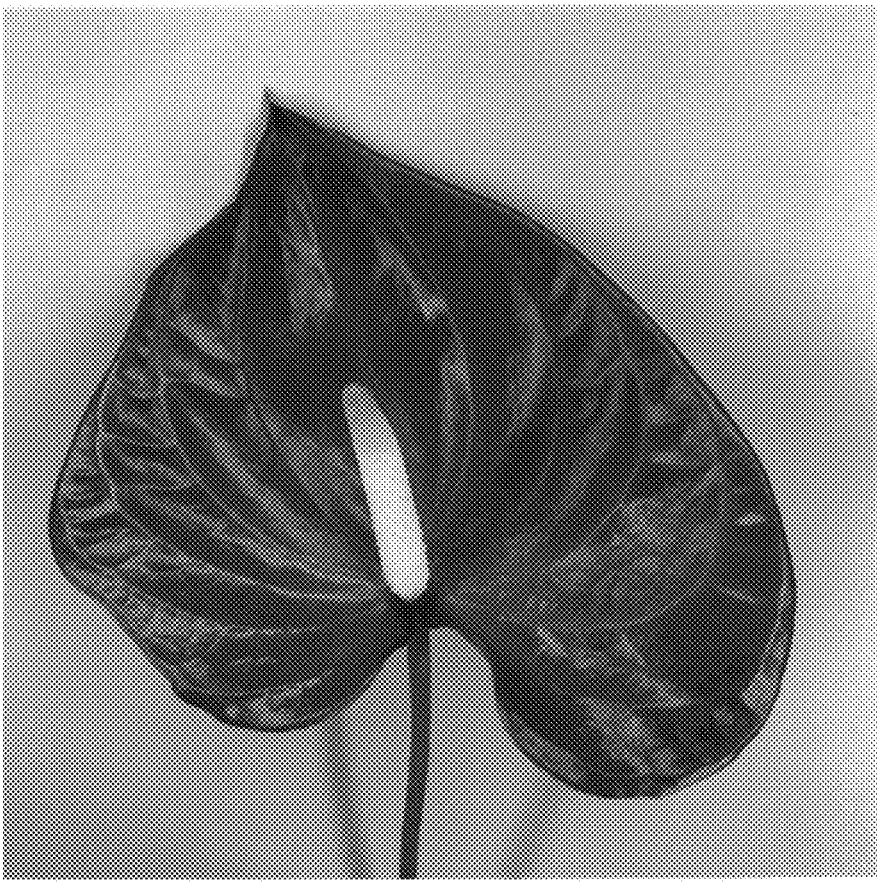
FIG. 2 shows a close-up of the mature spathe.
Figure 3:
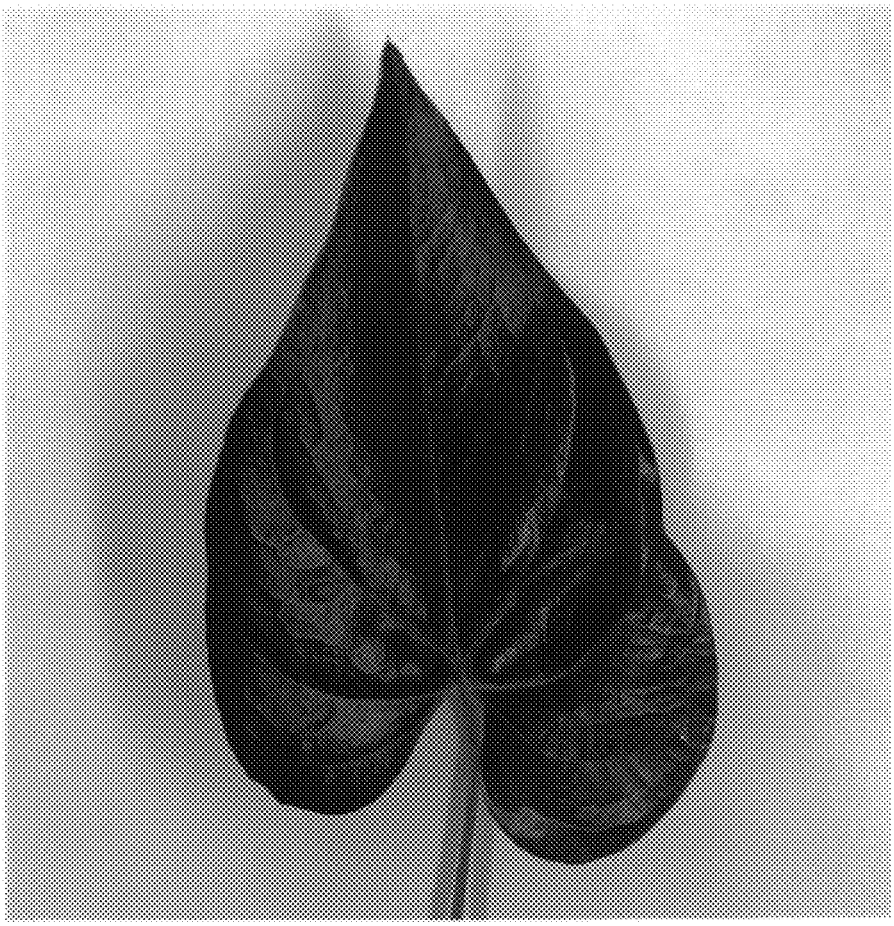
FIG. 3 shows a close-up of the upper leaf blade surface.

The following detailed description sets forth the distinctive characteristics of 'ANTHFYSAN'. The data which define these characteristics were collected from asexual reproductions carried out in Bleiswijk, the Netherlands. The plant history was taken on 44-week-old plants which were planted from tissue culture in 14-centimeter (diameter) pots and grown in a glass greenhouse between 19° C. and 24° C. Observations were made in November 2020. Color readings were taken under 5000 lux natural light in the greenhouse. Color references are primarily to The R.H.S. Colour Chart of The Royal Horticultural Society of London (R.H.S.) (2015).

DETAILED BOTANICAL DESCRIPTION

Classification:

*Family*.—Araceae.

*Botanical*.—*Anthurium andraeanum* L.

*Common name*.—*Anthurium*.

*Denomination*.—'ANTHFYSAN'.

Parentage:

*Female parent*.—*Anthurium* plant '16704-02' (unpatented).

*Male parent*.—*Anthurium* plant '20037-02' (unpatented).

Plant:

*Propagation*.—Tissue culture.

*Root description*.—Fleshy-creamy (RHS 62D) with a touch of pink (RHS 180D) colored roots with small hairy lateral roots having yellow (RHS 9A) colored root tips.

*Time to produce a finished flowering plant*.—42 to 46 weeks after planting in a 14-cm (diameter) pot.

*Growth habit*.—Upright.

*Height* (*measured from soil, including inflorescence*).—34.0 cm to 39.0 cm.

*Width* (*measured from leaf tips*).—39.0 cm to 44.0 cm.

Leaves:

*Immature leaves*.—Length: 16.0 cm to 19.0 cm. Width: 9.0 cm to 11.0 cm. Color: Upper surface: RHS N200A. Lower surface: RHS N199A with dark red margin (RHS 183B). Texture (both upper and lower surfaces): Glossy, leathery, and thin.

*Mature leaves*.—Length (fully expanded): 19.0 cm to 22.0 cm. Width: 12.0 cm to 14.0 cm. Shape: Cordate. Apex: Acuminate. Base: Cordate. Leaf blade angle with the petiole: Between 120 degrees and 140 degrees. Leaf margin: Entire. Color: Upper surface: RHS 147A. Lower surface: Something in between RHS N199A and 152A. Texture (both upper and lower surfaces): Weakly glossy, leathery, and thick. Venation: Pinnate veining; the mid-vein and primary veins (the veins that radiate out from the junction of petiole and leaf) protrude at the underside of the leaf blade. Venation color: Upper surface: RHS 146A. Lower surface: RHS 183B.

*Lobes*.—Present. Arrangement: Leaf blade has two lobes extending past the petiole. The lobes are non-touching. Length of lobes of mature leaf blades: 4.0 cm to 5.0 cm. Width of lobes of mature leaf blades: 5.0 cm to 6.0 cm. Distance from petiole/leaf junction to highest point on lobes of mature leaf blades: 5.0 cm to 6.0 cm.

*Petiole*.—Cross-section: Round. Diameter: 0.4 cm to 0.5 cm. Length: 22.0 cm to 25.0 cm for a mature leaf size. Color: Mature leaf: RHS 146B. Immature leaf: RHS 146C with a touch of red (RHS 181B). Cataphyll color surrounding the petiole: Outside: At the base RHS 180B and toward the tip RHS 180A. Inside: At the base RHS 180D and toward the tip RHS 180C.

*Geniculum*.—Length: 2.0 cm to 2.5 cm. Width: 0.4 cm to 0.5 cm. Color: RHS 144B.

Inflorescence:

*Arrangement*.—Single.

*Flowering habit* (*length of flowering season*).—Continuous.

*Number of inflorescences per plant*.—5 to 7.

*Fragrance*.—Absent.

*Longevity of inflorescence on plant*.—Over a year.

Spathe:

*Buds*.—The spathe is tightly rolled around the spadix and extrudes from the peduncle sheath.

*Arrangement*.—Spathe angle with the peduncle is between 120 degrees and 140 degrees; the spathe stands on a wiry peduncle about 0.0 cm to 3.0 cm below the foliage.

*Shape*.—Cordate.

*Apex*.—Acuminate.

*Base*.—Cordate.

*Texture*.—Weakly blistered.

*Margin*.—Undulated.

*Size*.—Length: 13.0 cm to 14.0 cm. Width: 11.0 cm to 12.0 cm.

*Lobes*.—Present. Arrangement: The spathe has two lobes extending past the peduncle. The lobes are non-touching. Length: 2.0 cm to 4.0 cm. Width: 4.0 cm to 5.0 cm.

*Color*.—Just fully open: Upper surface: RHS 185A. Lower surface: RHS 46A. This dark red color remains for a very long period, at least more than 30 weeks after opening. The spathe turns green after some weeks.

Peduncle:

*Shape*.—Erect.

*Cross-section*.—Round.

*Length*.—28.0 cm to 30.0 cm.

*Diameter*.—0.4 cm to 0.5 cm.

*Color*.—RHS 144B with a touch of RHS 178C toward the spathe.

Flowering time:

*General*.—One small, rooted, untreated tissue culture plant of 8.0 cm tall will flower, depending on the season, after 42 to 46 weeks and 5 to 6 blossoms appear. More blossoms appear after some additional weeks so that a full flowering and commercial plant will have 6 to 7 dark red spathes. Smaller blossoms may occur on immature plants.

Spadix:

*Size*.—Length: 4.0 cm to 4.5 cm (depending on flower size). Width (at apex): 0.5 cm to 0.6 cm. Width (at base): 0.7 cm to 0.8 cm.

*Shape*.—Columnar.

*Angle of spadix tip with peduncle*.—170 degrees to 180 degrees

*Texture*.—When the spathe is unfurling the spadix is smooth. When the spadix matures, small stigmata protrude. The stigmata are evenly distributed around the spadix. The spadix matures from base to top, slowly giving the spadix a somewhat rough appearance.

*Color*.—Immature: RHS 17B to RHS 153B toward the tip. Mature: RHS 158C. Ages to: RHS N144A.

Flowers:

*Quantity per spadix.*—160 to 200.

*Spadix flower arrangement.*—Bisexual, rounded in cross-section.

*Shape.*—Rounded.

*Size.*—Length: 0.05 cm to 0.10 cm. Diameter (maximum): 0.10 cm.

*Color.*—RHS 158C.

Reproductive organs:

*Stamens.*—Not visible.

*Pollen amount.*—Absent.

*Pistil.*—Quantity: Many. Length: Less than 0.01 cm. Color: RHS 158C.

*Style.*—Not observed to date.

*Stigma.*—Shape: Ovoid. Diameter: Less than 0.01 cm. Color: RHS 158C.

*Ovary.*—Rarely visible.

*Ovary color.*—Not measured.

Fruit and seed set: None observed to date.

Disease and pest resistance: No specific resistance or susceptibility observed to pathogens or pests common to *Anthurium* under commercial conditions to date.

COMPARISON WITH PARENTAL AND SIMILAR COMMERCIAL VARIETIES

'ANTHFYSAN' differs from the female parent plant '16704-02' (unpatented) in that 'ANTHFYSAN' has dark red spathes, whereas '16704-02' has brown spathes. Additionally, 'ANTHFYSAN' has wider spathes than '16704-02'.

'ANTHFYSAN' differs from the male parent plant '20037-02' (unpatented) in that 'ANTHFYSAN' has dark red spathes and an angle of the spadix tip with the peduncle that is 170 degrees to 180 degrees, whereas '20037-02' has red spathes and an angle of the spadix tip with the peduncle that is 140 degrees to 150 degrees.

'ANTHFYSAN' differs from similar commercial variety 'ANTHCUFPA' (U.S. Plant Pat. No. 28,032) in that 'ANTHFYSAN' has an angle of the spadix tip with the peduncle that is 170 degrees to 180 degrees, whereas 'ANTHCUFPA' has an angle of the spadix tip with the peduncle that is 140 degrees to 150 degrees. Additionally, 'ANTHFYSAN' has wider spathes than 'ANTHCUFPA'.

'ANTHFYSAN' differs from similar variety 'ANTHFUBE' (U.S. Plant Pat. No. 30,966) in that 'ANTHFYSAN' has red cataphylls and yellow immature spadices with greenish-yellow tips, whereas 'ANTHFUBE' has green cataphylls with red tips and green immature spadices.

I claim:

1. A new and distinct variety of *Anthurium* plant named 'ANTHFYSAN', substantially as illustrated and described herein.

* * * * *